United States Patent [19]

Hoy, Jr.

[11] Plant 4,886

[45] Sep. 14, 1982

[54] SEEDLING ROSE NO. 78-2R

[75] Inventor: Lowell L. Hoy, Jr., Richmond, Ind.

[73] Assignee: Joseph H. Hill Company, Richmond, Ind.

[21] Appl. No.: 222,492

[22] Filed: Jan. 5, 1981

[51] Int. Cl.[3] ..... A01H 5/00

[52] U.S. Cl. ..... Plt./21

[58] Field of Search ..... Plt./20, 21

*Primary Examiner*—Robert E. Bagwill

*Attorney, Agent, or Firm*—Chas. W. Rummler

[57] ABSTRACT

A new variety of hybrid tea rose for greenhouse culture and commercial production of cut flowers distinguished by its continuous and abundant production of large cardinal red flowers on long, strong stems; and its long and attractively pointed buds which, when half opened, display a flower having a high pointed center with the inner petals provided with a very desirable swirling effect and having a tendency to individually unfurl until the flower is fully opened thereby displaying a center of many yellow stamens which enhances and accentuates the velvety iridescence of the redness in the opened flower. This new plant has a vigorous, much branched growth habit and a moderately abundant production of medium large leaves and of strong, large diameter canes.

1 Drawing Figure

BACKGROUND OF THE NEW PLANT

My new red rose cultivar is the result of my breeding efforts carried on at Richmond, Ind., with the object of producing a more distinctive and classical bud and open flower with improved stem length, productivity, resistance, and vase life as a commercial cut flower. This seedling resulted from my crossing "Love Affair", U.S. Plant Pat. No. 3,287, and an unnamed and unpatented seedling which possessed excellence of stem, foliage, flower and disease resistance that was desired to be captured in the new plant. This was successfully accomplished in the new seedling, as well as an improved color compared to that of the seed parent. This crossing was done in the Spring of 1976 and the first flowers appeared in the Fall of 1977. The beauty of this flower and the excellent characteristics of the plant led to my propagating the new plant for observation and test and this was done by budding at Richmond, Ind. Subsequent propagation by budding through successive generations has shown that the desired and novel characteristics of this plant hold true from generation to generation and appear to be firmly fixed.

DESCRIPTION OF THE DRAWING

This new variety of rose plant is illustrated by the accompanying photographic drawing which shows, in full color, several stages of the bud opening, a newly opened flower, top and under side views of typical leaves, specimens of young and old wood, and typical petals of a newly opened flower and of a three day opened flower, the colors shown being as nearly true as can be reasonably obtained by careful conventional photographic procedures.

DESCRIPTION OF THE NEW PLANT

The following is a description, in detail, of my new rose plant variety with color designations according to Koster's Color Guide (K), and the Robert S. Wilson Horticultural Colour Chart (W) issued by The British Colour Council in collaboration with The Royal Horticultural Society of London, England, the following data being from observations of greenhouse plants grown at Richmond, Ind.

THE PLANT

Origin: Seedling.

Parentage:

*Seed parent.*—Love Affair (U.S. Plant Pat. No. 3,287).

*Pollen parent.*—An unknown seedling.

Classification: Hybrid Tea.

Form: Bush.

Habit: Upright and much branched.

Growth: Free and vigorous.

Canes: Strong and of large diameter.

Main stems:

*Color.*—Spinach Green, 0960/3 (W).

*Thorns.*—Several of medium length and hooked downwardly from a short, broad base. Color: Lettuce Green, 861/3, shaded with Spinel Red, 0023/1 (W).

*Prickles and hairs.*—None.

Branches:

*Color.*—Spinach Green, 0960/1 (W).

*Thorns.*—Several of medium length hooked downwardly from a short, broad base. Color: Lilac, Plate No. 48 (K).

*Prickles.*—Very few. Color: Mahogany, Plate No. 95 (K).

*Hairs.*—None.

New shoots:

*Color.*—Erythrite Red, 0027/1 (W).

*Thorns.*—Several of medium length and hooked downwardly from a short, narrow base. Color: Erythrite Red, 0027 (W).

*Prickles.*—Few. Color: Erythrite Red, 0027 (W).

*Hairs.*—None.

Foliage:

*Quantity.*—Moderately abundant.

*Leaves.*—Size: Medium large. Shape: Odd pinnate.

*Leaflets.*—3, 5 and 7 in number. Shape: Ovoid with obtuse base, acuminate apex and simply serrate margins. Color: Mature leaf: Upper surface — closest color Spinach Green, 0960 (W). Under surface — Spinach Green, 0960/1 (W). Young leaf: Upper surface — Spinach Green, 0960/3 (W). Under surface — Agathia Green, 60/3, striped with Spinel Red, 0023/1 (W). Aspect: Glossy. Texture: Leathery.

*Rachis.*—Medium heavy with smooth, grooved upper side and moderately smooth and prickly under side.

*Stipules.*—Of medium length and width with points of medium length turning outwardly at an angle of more than 45° to 90° with tips recurved toward the stem.

THE BUD

Before the calyx breaks:

*Size.*—Medium large.

*Form.*—Long pointed with a conspicuous neck and foliaceous appendages on the surface of the bud, some with bristle-like foliaceous parts extending beyond the tip of the bud a distance equal to one-fourth or more of the bud length.

*Color.*—Scheeles Green, 860/3, shaded with Scheeles Green 860/1 (W).

As the calyx breaks:

*Color (outside of petal).*—Oxblood Red, 00823/2 (W).

As the first petals open:

*Bud size.*—Medium large.

*Bud form.*—Long pointed.

*Color.*—Outside — Crimson Carmine, Plate No. 41 (K). Inside — Cardinal Red, 822/3 (W).

*Bud opening.*—The bud opens up well in the greenhouse.

*Sepals.*—Permanent and of medium length. Form: Spear-shaped and curled. Color: Inside — Pod Green, 061/1 (W). Outside — Spinach Green, 0960/2 (W).

*Peduncle.*—Medium strong and of medium length and diameter. Bark: Entirely smooth. Color: Scheeles Green, 860/2 (W). Thorns, prickles and hairs: None.

THE FLOWER

Blooming habit: Continuous, free and abundant.

Borne: 1, 2 or 3 per stem on very strong and long stems.

Size:

*When fully opened.*—Large, about 4 to 4½ inches in diameter.

Form: Full and high centered at first, with the petals remaining tightly rolled inward, becoming open and high centered with the petals loosely rolled outward at maturity.

Petalage: Double with 20 to 25 petals arranged irregularly, but the stamens are not hidden.

*Shape of petals.*—Outside petals — round with obtuse apex and with one notch. Intermediate petals — round with obtuse apex. No notches noted. Inside petals — ovate with obtuse apex. No notches noted.

*Texture.*—Moderately thick.

*Aspect.*—Velvety on both inside and outside petal surfaces.

Color of petals:

A. The following observations were made of a newly opened greenhouse grown flower in October 1980.

*Outside petals.*—Outside surface: Crimson Carmine, Plate No. 41 (K), slightly blotched at the base with Sulphur Yellow, 1/3 (W). Inside surface: Cardinal Red, 822/2 (W), slightly blotched at the base with Sulphur Yellow, 1/2 (W).

*Intermediate petals.*—Outside surface: Crimson Carmine, Plate No. 41 (K), slightly tinted at the base with Sulphur Yellow, 1/3 (W). Inside surface: Cardinal Red, 822/2 (W), slightly tinted at the base with Sulphur Yellow, 1/3 (W).

*Inner petals.*—Outside surface: Crimson Carmine, Plate No. 41 (K), slightly tinted at the base with Dresden Yellow, 64/3 (W). Inside surface: Cardinal Red, 822/2 (W), slightly tinted at the base with Dresden Yellow, 64/3 (W).

B. The following observations were made of a flower that was opened for three days in a greenhouse in October 1980.

*All petals.*—Outside surface: Cardinal Red, 822/3 (W), slightly blotched at the base with Primrose Yellow, 601/2 (W). Inside surface: Cardinal Red, 822/2 (W), slightly blotched at the base with Naples Yellow, 403/1 (W).

General color effect of the open bloom:

*Newly opened flower.*—Cardinal Red, 822/3 (W).

*Flower opened three days.*—Cardinal Red, 822/2 (W).

Persistence: Petals hang on and dry.

Fragrance: Moderate.

Lasting quality: 6 to 7 days for the fully opened flower kept at living room temperature in October.

REPRODUCTIVE ORGANS

Stamens: Many in number arranged irregularly about the pistils and tucked in the calyx.

*Anthers.*—Medium large in size. Color: Eygptian Buff, 407/1 (W).

*Filaments.*—Medium length, most with anthers. Color: Geranium Lake, 20/2 (W).

*Pollen.*—Abundant. Color: Cadmium Orange, 8/1 (W).

Pistils: Medium in number.

*Styles.*—Of medium length and uneven. Medium heavy in size and bunched. Color: Amber Yellow, 505/1 (W).

*Stigmas.*—Color — Amber Yellow, 505 (W).

Ovularies: Encased in calyx.

Hips and seeds: None observed.

This new rose variety most nearly resembles the rose cultivar "Samantha" (U.S. Plant Pat. No. 3,727) inasmuch as the color of the flower is comparable; however, the foliage of this new variety is larger and more abundant and the new plant is easier to time for cropping in the greenhouse under controlled environmental conditions.

With respect to its seed parent, my new rose cultivar has the advantage that the flower is borne on longer stems thereby requiring less pinching to produce desirable cut flower lengths for the commercial cut flower market. Also, the foliage of the new plant is leathery and abundant throughout the entire length of the stem and the flower color is more brilliant and does not tend to turn blue during living room temperature vase-life of six to seven days. Furthermore, the half-opened flower of this new plant has a high pointed center with the inner petals having a very desirable swirling effect and these inner petals have a tendency to individually unfurl progressively until the flower is fully opened to display a center of many yellow stamens which enhance and accentuate the velvety iridescence of the redness in the open flower.

I claim:

1. A new and distinct variety of rose plant substantially as herein shown and described; characterized, in particular, by its free, abundant and continuous production of flowers borne on long, strong stems and which have an improved vase life; its moderately abundant production of medium large leaves throughout the entire length of the stem; and by its vigorous and much branched growth habit.

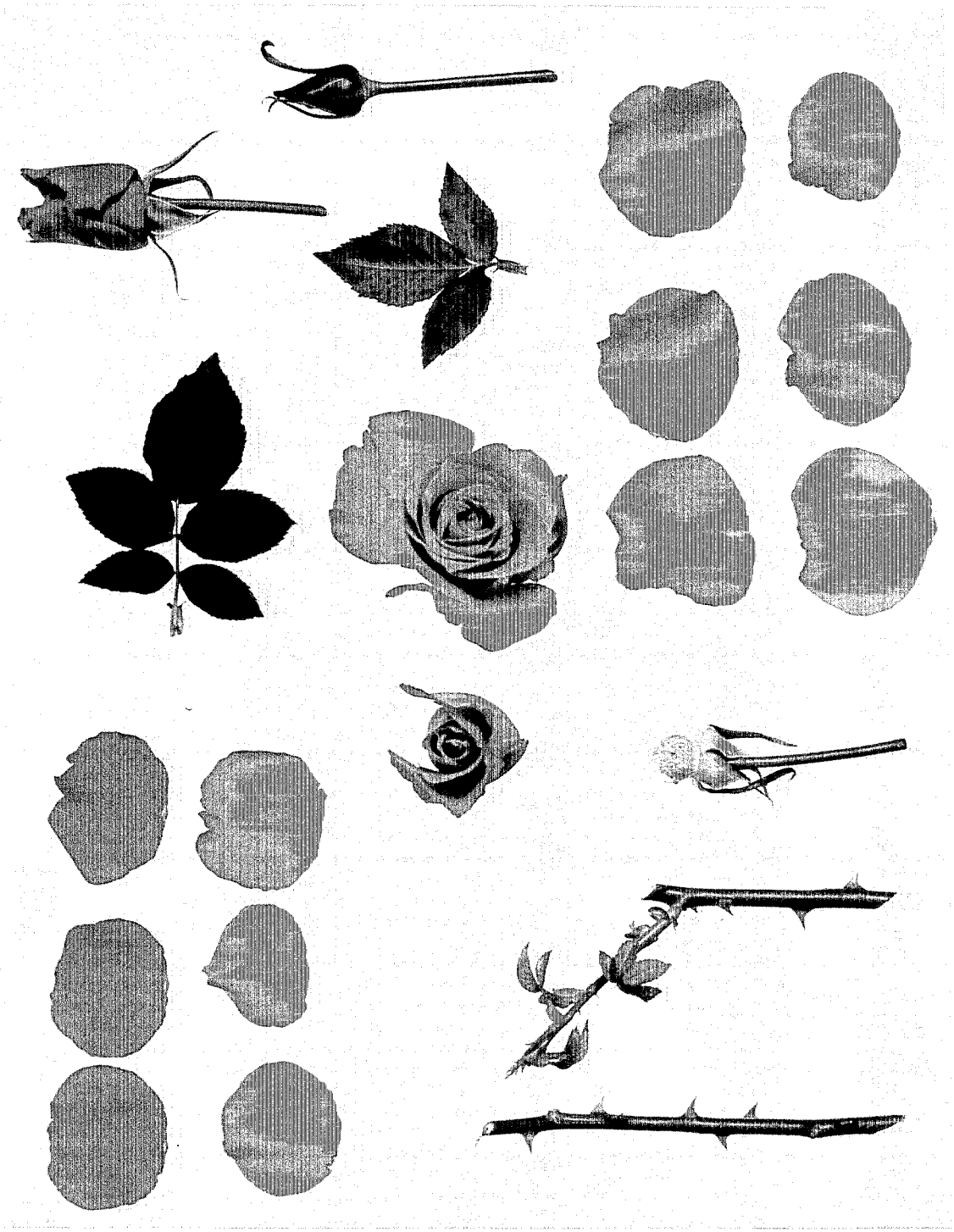

* * * * *